United States Patent
Lynch

(10) Patent No.: US 10,314,868 B2
(45) Date of Patent: Jun. 11, 2019

(54) PROBIOTIC DELIVERY SYSTEMS

(71) Applicant: ProbioTech LLC, Princeton, NJ (US)

(72) Inventor: Deborah L. Lynch, Princeton, NJ (US)

( * ) Notice: Subject to any disclaimer, the term of this patent is extended or adjusted under 35 U.S.C. 154(b) by 22 days.

(21) Appl. No.: 15/453,348

(22) Filed: Mar. 8, 2017

(65) Prior Publication Data

US 2017/0173091 A1    Jun. 22, 2017

Related U.S. Application Data

(63) Continuation of application No. PCT/US2016/061372, filed on Nov. 10, 2016.

(60) Provisional application No. 62/366,780, filed on Jul. 26, 2016, provisional application No. 62/303,118, filed on Mar. 3, 2016, provisional application No. 62/253,535, filed on Nov. 10, 2015.

(51) Int. Cl.

| | | |
|---|---|---|
| *A61K 35/747* | (2015.01) | |
| *A61K 45/06* | (2006.01) | |
| *A61K 9/00* | (2006.01) | |
| *A61K 9/02* | (2006.01) | |
| *A61K 9/48* | (2006.01) | |
| *A61K 35/741* | (2015.01) | |
| *A61K 35/744* | (2015.01) | |
| *A61K 35/745* | (2015.01) | |
| *A61K 47/02* | (2006.01) | |
| *A61K 47/12* | (2006.01) | |
| *A61K 47/44* | (2017.01) | |
| *A61K 47/46* | (2006.01) | |
| *A61K 38/06* | (2006.01) | |
| *A61K 36/87* | (2006.01) | |
| *A61K 36/53* | (2006.01) | |
| *A61K 36/63* | (2006.01) | |

(52) U.S. Cl.
CPC .......... *A61K 35/747* (2013.01); *A61K 9/0031* (2013.01); *A61K 9/0036* (2013.01); *A61K 9/0053* (2013.01); *A61K 9/02* (2013.01); *A61K 9/48* (2013.01); *A61K 35/741* (2013.01); *A61K 35/744* (2013.01); *A61K 35/745* (2013.01); *A61K 36/53* (2013.01); *A61K 36/63* (2013.01); *A61K 36/87* (2013.01); *A61K 38/063* (2013.01); *A61K 45/06* (2013.01); *A61K 47/02* (2013.01); *A61K 47/12* (2013.01); *A61K 47/44* (2013.01); *A61K 47/46* (2013.01)

(58) Field of Classification Search
CPC .... A61K 35/747; A61K 45/06; A61K 9/0031; A61K 9/0036; A61K 9/0053; A61K 35/741; A61K 35/74
USPC .......................... 424/408, 433, 435, 436, 455
See application file for complete search history.

(56) References Cited

U.S. PATENT DOCUMENTS

| | | | |
|---|---|---|---|
| 4,347,237 A | 8/1982 | Evenstad et al. | |
| 8,361,497 B2 | 1/2013 | Miller | |
| 8,802,161 B2 | 8/2014 | Mazzio et al. | |
| 8,853,269 B2 | 10/2014 | Mosbaugh et al. | |
| 2005/0191346 A1* | 9/2005 | Nowak | A61J 3/07 424/451 |
| 2008/0274162 A1* | 11/2008 | Nessa | A61K 9/0031 424/436 |
| 2013/0209612 A1 | 8/2013 | Michalowski et al. | |

FOREIGN PATENT DOCUMENTS

| | | |
|---|---|---|
| CN | 102475887 A | 5/2012 |
| FR | 3008317 A1 | 1/2015 |

OTHER PUBLICATIONS

Anonymous. Prebiotics/Probiotics; The University of North Dakota Dining Services (2010) downloaded from: https://www.und.edu/student-life/dining/_files/docs/fact-sheets/probiotics.pdf on Jun. 30, 2017.*
Anonymous. Typical Fatty-Acid Compositions of Some Common Fats; (2016) downloaded from: http://www.web.pdx.edu/~wamserc/C336S12/fat.pdf on Jun. 30, 2017.*
Hidaka et al. Effects of Fructooligosaccharides on Intestinal Flora and Human Health; Bifidobacteria Microflora, vol. 5, No. 1 pp. 37-50. (Year: 1986).*

* cited by examiner

*Primary Examiner* — Paul C Martin
(74) *Attorney, Agent, or Firm* — Saul Ewing Arnstein & Lehr LLP; Justin W. Crotty

(57) ABSTRACT

Suppository compositions are provided combining a pharmaceutically acceptable matrix material that is solid outside of the human body and in a dry environment, but which melts at body temperature; and apple cider vinegar and one or more species of probiotic bacteria dispersed within the matrix material; wherein the matrix material contains a mixture of fatty acids that are solid at room temperature. Methods for supplementing and nourishing the microbiome of the rectum of a male or female and the microbiome of the vagina of a female are also disclosed. Oral dosage forms of the compositions of the present invention are also provided.

17 Claims, 1 Drawing Sheet

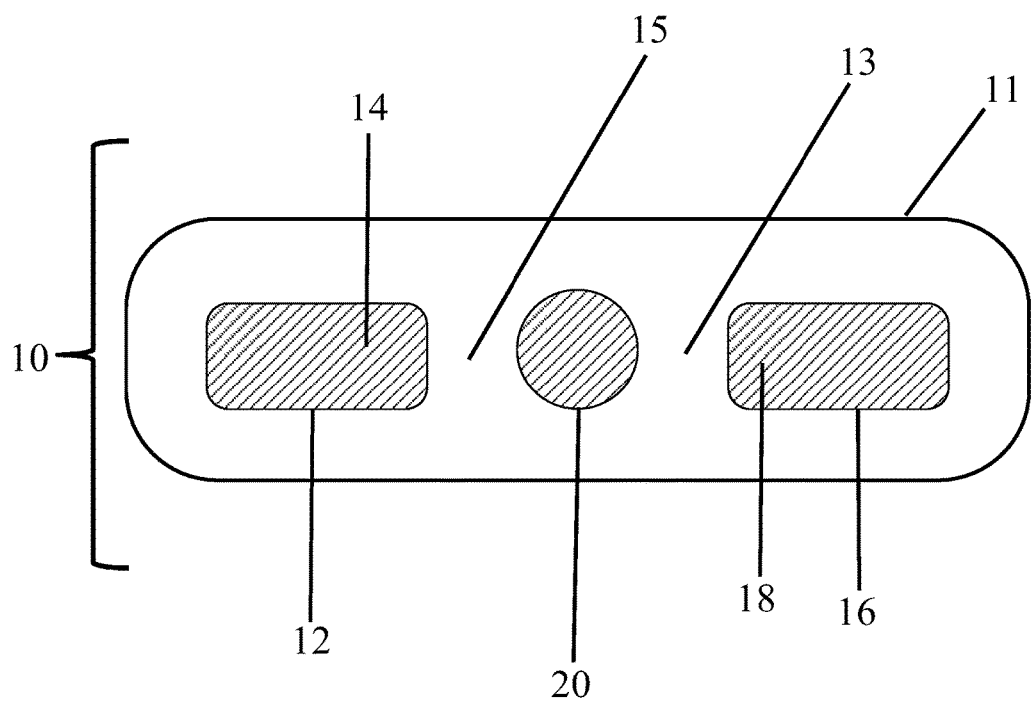

PROBIOTIC DELIVERY SYSTEMS

CROSS-REFERENCE TO RELATED APPLICATIONS

The present application is a Continuation of International Patent Application No. PCT/US2016/061372, filed Nov. 10, 2016, which claims priority benefit under 35 U.S.C. § 119(e) of U.S. Patent Application Ser. Nos. 62/253,535 filed Nov. 10, 2015; 62/303,118 filed Mar. 3, 2016 and 62/366,780 filed Jul. 26, 2016. The disclosures of all four applications are incorporated herein by reference.

BACKGROUND OF THE INVENTION

Each human is a microbial laboratory, harboring an ecosystem of microbes whose numbers are greater than the total number of human cells in the body. In fact, for every one human cell there are approximately 10 microbial cells. The collective genome of the microbes living within each human is at least 150 times larger than the genome of the human that they inhabit.

The first phase of the Human Microbiome Project, under the auspices of the National Institutes of Health, was completed in 2012. This multimillion-dollar research program was funded to catalogue and better define the microbes that inhabit the living human. Significant findings from this research include: 1) the microbiome is not the same among all humans, but varies dramatically from one individual to the next. 2) The microbiome of the individual also can change quickly over time, depending on the circumstances of the individual (diet, environment, drugs, etc.). 3) The largest number of microbes in the human inhabit the gastrointestinal tract. Further, the highest concentration of these microbes is found in the large intestines. 4) The large intestines can be described as a digestion chamber for the human. In this area, the microbiome of organisms, mainly utilizing anaerobic (needing no oxygen) bacteria, break down the foods for either absorption or elimination. 5) The composition of each individual's microbiome is closely linked to that person's immune function. 6) In addition to a healthy microbiome promoting health, this 'healthy' microbiome appears to be essential for cultivating a growth or a 'farm' of human friendly microbes that sustain health.

Thus, the human gastrointestinal tract has trillions of microbes that are living in the intestinal track from the mouth to the rectum and appear to play a major role in the health and disease of each individual. Microflora is going to revolutionize our understanding of health and disease. For example, research has shown in human and animal models that those who have an elevated body mass index in the obese range and/or who have type 2 diabetes appear to have a different bacterial milieu than those without these conditions. In fact, when the microbiota from obese humans or animals are transferred to healthy animals of average weight, but devoid of bacteria of their own, these recipient animals appear to have a greater risk of eventually becoming obese or diabetic. In addition, rheumatoid arthritis, muscular dystrophy, multiple sclerosis, depression, fibromyalgia, and possibly some cancers may be linked to an altered or unfavorable microbiome. However, one of the major issues is how to populate humans with a microbiome that may be able to support or restore health. This is a medical issue that has been challenging.

To date, the three major ways of delivering 'healthy' or desirable bacteria to the human in an attempt to promote health are:

1. Through food and drinks. Many products such as prebiotics and probiotics are currently marketed with this claim. Probiotics are found in foods such as certain yogurts and kefirs, while prebiotics are found in whole grains, bananas, onions, garlic, honey and artichokes. In addition, probiotics and prebiotics are added to some foods and available as dietary supplement. In addition, everyday foods such as miso, sauerkraut, pickles, kimchi, Kombucha tea and other fermented foods may contribute to promote a healthy intestinal microbiome.

2. Through capsules and tablets that are taken by mouth and contain these organisms known as probiotics. Some brands are available with live bacteria. Most commercial brands suggest they have a range of million to billions of bacteria strains because the delivery system breaks down so much of bacteria through the gastric acids in our stomachs. The amounts delivered are actually unknown. Each of the foregoing methods lacks the ability to directly deliver bacteria to the rectal area or the vaginal area. Studies have suggested that bacteria or probiotics may impact the function of colonizing microbes. Other studies suggest that supplementing bacteria via probiotics may promote homeostasis of the gut microbiota rather than change its composition. Each of the foregoing methods lacks the ability to directly deliver bacteria to the rectal area or the vaginal area. Studies have suggested that bacteria or probiotics may impact the function of colonizing microbes. Other studies suggest that supplementing bacteria via probiotics may promote homeostasis of the gut microbiota rather than change its composition.

3. Through fecal microbiota transplant (FMT), the process of transplantation of fecal bacteria matched from a healthy individual into an unhealthy recipient. FMT involves restoration of the colonic microflora by introducing healthy bacterial flora through infusion of donor stool, e.g. by enema, orogastric tube, by mouth, or by other implantation means, in the form of a capsule containing freeze-dried material, obtained from a healthy donor. Previous terms for the procedure include fecal bacteriotherapy, fecal transfusion, fecal transplant, stool transplant, fecal enema, and human probiotic infusion (HPI). Because the procedure involves the complete restoration of the entire fecal microbiota, not just a single agent or combination of agents, these terms have now been replaced by the new term fecal microbiota transplantation. However, current procedures at best provide stool samples with an approximate match for the microbiome needs of a patient.

There remains a need for a personalized medicine approach to maintaining a healthy microbiome for individual patients.

SUMMARY OF THE INVENTION

This need is met by the present invention. With the advancement of science today the present invention provides a process for delivering healthy bacteria to the rectum and vagina by the use of a suppository delivery system modeled after rectally and vaginally inserted products. The rectal and vaginal suppositories of the present invention contain bacteria that are desirable for the human microbiome of the lower gastrointestinal tract. The rectal and vaginal suppositories are compounded to not only supplement the microbes inhabiting the vagina and rectum but also to nourish the microbiome. The rectal suppository is used by digital insertion through the anus into the rectum, thereby bypassing the stomach and upper intestines. The vaginal suppository is used by digital insertion through the introitus therefore bypassing the stomach and upper intestines. The described suppositories in this invention will be inserted by the user in the same manner that over the counter rectal suppositories, or vaginal suppositories insertion that are used.

With regard to the rectal suppository, the intestines are a long, continuous tube running from the stomach to the anus. Most absorption of nutrients and water happen in the intestines. The intestines include the small intestine, large intestine, and rectum. The large intestine performs the vital functions of converting food into feces, absorbing essential vitamins produced by gut bacteria. Bacterial fermentation converts the chyme into feces and releases vitamins, including vitamins K, B1, B2, B6, B12, and biotin. Vitamin K is almost exclusively produced by the gut bacteria and is essential in the proper clotting of blood. Gases such as carbon dioxide and methane are also produced as a byproduct of bacterial fermentation and lead to flatulence, or gas passed through the anus. The digestive system, including the mouth, esophagus, stomach, small intestine and colon, make up one long tube that must act like the skin to protect the blood and inner organs against harmful materials. In fact, the lining of the digestive passageway is continuous with the skin at the mouth and anus, making the skin and the lining of the digestive passageway one continuous barrier that protects the blood and inner organs against harmful substances in the environment. There are data that suggest the microbiome in the rectal area of the gastrointestinal tract assists in maintaining a healthy immune system in both males and females, which the present invention accomplishes by inserting bacteria directly into the rectum.

According to one aspect of the present invention, a suppository composition is provided for the delivery of probiotic bacteria and nutritional supplements to the rectum or vagina to supplement and nourish the existing microbiome, wherein the composition includes the following ingredients:

a) a pharmaceutically acceptable fatty acid matrix that melts at body temperature;

b) one or more species of probiotic bacteria dispersed within the fatty acid matrix;

c) a source of nutrients for the probiotic bacteria; and d) a pH stabilizing agent;

wherein the matrix material comprises a mixture of fatty acids that are solid at room temperature.

According to one embodiment, the source of nutrients is apple cider vinegar. According to another embodiment, the nutrients include one or more nutrients selected from iron, calcium, potassium, vitamin B12, vitamin C and vitamin K.

According to another embodiment, the composition includes an anti-fungal agent.

According to one embodiment, the pH stabilizing agent is citric acid, Vitamin C or sodium bicarbonate. According to another embodiment, the mixture of fatty acids contains at least 90 wt % saturated fatty acids. According to another embodiment, at least 50 wt % of the saturated fatty acids of the mixture of fatty acids is lauric acid. According to another embodiment, the mixture of fatty acids includes coconut oil. In yet another embodiment, the mixture of fatty acids contains shea butter.

According to one embodiment, the composition further includes one or more anti-inflammatory nutritional supplements selected from Vitamin A, Vitamin $B_6$, Vitamin D, Vitamin $K_2$ (MK 1), potassium, folic acid, L-carnitine, quercetin, magnesium, calcium, alpha-lipoic acid, fiber, omega-3 fatty acids, Nuclear factor-like 2 (NRF2) activators, L-glutathione, L-glutamate and gamma-aminobutyric acid (GABA) dispersed within said matrix material.

In yet another embodiment, the suppository composition further includes one or more items selected from lemon juice, lactic acid, chamomile (fresh or oil), coenzyme Q-10, collagen, aloe or aloe inner leaf gel or extract, gelatin, green tea extract, lactose, galactose, fructose, fructose oligosaccharides, isomaltose, dextrose, glucose, amylopectin, inulin, resistant starch, corn starch, oligosaccharides, rosemary leaf extract, oregano oil, curcumin, coffee, ginger, petroleum jelly, mineral oil, shark liver oil, flax seed oil, sodium chloride, green barley, agrimony, aniseed-basil, aniseed-fennel, cayenne, *Echinacea*, garlic, honey, molasses, horseradish, lavender, marshmallow, olive oil, milk, peppermint, slippery elm, buttermilk, goldenrod, St John's wort, uva ursi, yarrow, bee pollen, bee propolis, mint and the like.

In another embodiment, the probiotic bacteria include one or more bacteria family or genus selected from *Lactobacillus rhamnosus, Bifidobacterium lactis, Lactobacillus planetarium, Lactobacillus acidophilus, Lactobacillus brevis, Bifidobactrium longum, Lactobacillus salvarius, Lactobacillus casei, Bifidobacterium bifidum*, and the like.

In yet another embodiment, the matrix optionally further includes one or more pharmaceutically acceptable items selected from polyethylene glycol, hydrogels, cocoa butter, glycerinated gelatin, shea butter, petrolatum, mineral oil, shark liver oil, and the like.

In yet another embodiment, a suppository delivery system is provided containing the matrix material of the present invention without probiotic bacteria. Such a system can be used for delivery by suppository of essentially any active agent or nutritional supplement. Therefore, according to one aspect of the present invention, a suppository composition is provided containing a pharmaceutically acceptable matrix material that is solid at room temperature and in a dry environment, but which melts at body temperature; and a source of nutrients for the microbiome of the large intestine; wherein the matrix material contains a mixture of fatty acids that are solid at room temperature.

According to one embodiment, the source of nutrients includes apple cider vinegar. According to another embodiment, the mixture of fatty acids contains at least 90 wt % saturated fatty acids. According to another embodiment, at least 50 wt % of the saturated fatty acids of the mixture of fatty acids is lauric acid. According to another embodiment, the mixture of fatty acids includes coconut oil. In yet another embodiment, the mixture of fatty acids contains shea butter.

In yet another embodiment, the suppository matrix optionally further includes one or more pharmaceutically acceptable items selected from polyethylene glycol, hydrogels, cocoa butter, glycerinated gelatin, and the like.

In one embodiment, the composition further includes one or more anti-inflammatory nutritional supplements selected from Vitamin A, Vitamin B6, Vitamin D, Vitamin K2 (MK 1), potassium, folic acid, L-carnitine, quercetin, magnesium, calcium, alpha-lipoic acid, fiber, omega-3 fatty acids, Nuclear factor-like 2 (NRF2) activators, L-glutathione, L-glutamate and gamma-aminobutyric acid (GABA) dispersed within said matrix material.

In yet another embodiment, the suppository composition further includes one or more items selected from lemon juice, lactic acid, chamomile (fresh or oil), coenzyme Q-10, collagen, aloe or aloe inner leaf gel or extract, gelatin, green tea extract, lactose, galactose, fructose, fructose oligosaccharides, isomaltose, dextrose, glucose, amylopectin, inulin, resistant starch, corn starch, oligosaccharides, rosemary leaf extract, oregano oil, curcumin, coffee, ginger, petroleum jelly, mineral oil, shark liver oil, flax seed oil, sodium chloride, green barley, agrimony, aniseed-basil, aniseed-fennel, cayenne, *Echinacea*, garlic, honey, molasses, horseradish, lavender, marshmallow, olive oil, milk, peppermint, slippery elm, buttermilk, goldenrod, St John's wort, uva ursi, yarrow, bee pollen, bee propolis, mint and the like.

According to another aspect of the present invention, a dosage form is provided for the delivery of probiotic bacteria and nutritional supplements to the gastrointestinal tract to supplement and nourish the existing microbiome, wherein the dosage form is a multi-chamber capsule with a first chamber containing one or more species of probiotic bacteria dispersed within the fatty acid matrix and a second chamber containing nutritional supplements for the probiotic bacteria and for the existing microbiome. The capsules can be hard or soft and can be made from gelatin or vegetable materials. The dosage form may contain two, three or four chambers, or more. They can be coated with an enteric coating formulated to dissolve at a predetermined gastrointestinal location.

In one embodiment the dosage form is an oral dosage form. In another embodiment it is a suppository.

According to one embodiment, the source of nutrients includes apple cider vinegar. According to another embodiment, the mixture of fatty acids contains at least 90 wt % saturated fatty acids. According to another embodiment, at least 50 wt % of the saturated fatty acids of the mixture of fatty acids is lauric acid. According to another embodiment, the mixture of fatty acids includes coconut oil. In yet another embodiment, the mixture of fatty acids contains shea butter.

In yet another embodiment, the suppository matrix optionally further includes one or more pharmaceutically acceptable items selected from polyethylene glycol, hydrogels, cocoa butter, glycerinated gelatin, and the like.

In one embodiment, the composition further includes one or more anti-inflammatory nutritional supplements selected from Vitamin A, Vitamin B6, Vitamin D, Vitamin K2 (MK 1), potassium, folic acid, L-carnitine, quercetin, magnesium, calcium, alpha-lipoic acid, fiber, omega-3 fatty acids, Nuclear factor-like 2 (NRF2) activators, L-glutathione, L-glutamate and gamma-aminobutyric acid (GABA) dispersed within said matrix material.

In yet another embodiment, the suppository composition further includes one or more items selected from lemon juice, lactic acid, chamomile (fresh or oil), coenzyme Q-10, collagen, aloe or aloe inner leaf gel or extract, gelatin, green tea extract, lactose, galactose, fructose, fructose oligosaccharides, isomaltose, dextrose, glucose, amylopectin, inulin, resistant starch, corn starch, oligosaccharides, rosemary leaf extract, oregano oil, curcumin, coffee, ginger, petroleum jelly, mineral oil, shark liver oil, flax seed oil, sodium chloride, green barley, agrimony, aniseed-basil, aniseed-fennel, cayenne, *Echinacea*, garlic, honey, molasses, horseradish, lavender, marshmallow, olive oil, milk, peppermint, slippery elm, buttermilk, goldenrod, St John's wort, uva ursi, yarrow, bee pollen, bee propolis, mint and the like.

In another embodiment, the probiotic bacteria include one or more bacteria family or genus selected from *Lactobacillus rhamnosus, Bifidobacterium lactis, Lactobacillus planetarium, Lactobacillus acidophilus, Lactobacillus brevis, Bifidobactrium longum, Lactobacillus salvarius, Lactobacillus casei, Bifidobacterium bifidum*, and the like.

The present invention is used to nourish and/or supplement the microbiome of the human lower gastro-intestinal tract with desirable bacteria. Therefore, according to another aspect of the present invention, a method is provided for modifying by supplementing or through nourishment provided to the existing gut bacteria in the microbiome of the rectum by inserting into the rectum the suppository compositions of the present invention.

The compositions of the present invention provide an alternative to fecal microbiota transplantation in which the transplanted probiotics can be selected and quantities tittered to address the needs of an individual patient's microbiome. This represents an improvement over existing treatments in which clinicians attempt to match the bacterial profile of donor stool to the microbiome needs of a patient. Therefore, according to another aspect of the present invention, a microbiota transplantation method is provided for a patient in need thereof, in which a composition according to the present invention is formulated to supply the microbiome needs of a particular patient and then administered to the gastrointestinal tract of the patient.

While intended primarily for the introduction of desirable bacteria into the lower gastro-intestinal tract microbiome of men and woman, via the rectum, the present invention, when inserted into the vagina, may be used for supplementing or nourishing the bacteria of the vagina. Therefore, according to another aspect of the present invention, a method is provided for delivering desirable bacteria and/or supplying nourishment into the microbiome of the vagina by the woman inserting into her vagina the suppository composition of the present invention.

BRIEF DESCRIPTION OF THE DRAWING

FIG. 1 depicts a three compartment oral dosage or rectal dosage form according to one embodiment of the present invention.

DETAILED DESCRIPTION

Data suggest that the bacteria in the lower gastrointestinal system have a direct inter-action with human health. There are two kinds of nourishment: nourishment of the human body and the nourishment of the existing microbiome cells. Because of this, there appears to be a direct link to the bacteria in the rectal mucosa of humans and their ability to prevent disease or be more susceptible to disease. Therefore, by providing the rectum with healthy bacteria via a rectal suppository or providing nourishment to the existing bacteria present in the human gut, the consumer will populate the intestinal mucosa with desirable bacteria and nourish them. In this way, the suppository of the present invention can promote and support overall human health.

The suppository compositions of the present invention contain a pharmaceutically acceptable matrix material that is solid outside of the human body and in a dry environment, but which melts at body temperature and when in contact with mucosa of the rectum or vagina following insertion. One or more species of probiotic bacteria are dispersed within this matrix with PH stabilizing agents such as sodium bicarbonate and citric acid, and with nutrients for the probiotic bacteria, such as the nutrients found in apple cider vinegar, as well as Vitamin B12, Vitamin C, Vitamin K, and the like. The suppository composition is designed so that the matrix material melts and dissolves within the rectum or vagina to release the probiotic material and the other beneficial ingredients.

The matrix material is based on a mixture of fatty acids that are solid at room temperature. For purposes of the present invention, "room temperature" is defined as an indoor temperature of approximately 70° F. According to one embodiment the mixture of fatty acids contains at least 90 wt % saturated fatty acids. Suppository compositions according to the present invention will contain between about 30 and about 90 wt % matrix materials. In one embodiment, suppository compositions are provided containing between about 40 and about 75 wt % of the matrix material. In another embodiment, suppository compositions are provided containing between about 45 and about 60 wt % of the matrix material.

According to one embodiment at least 50 wt % of the saturated fatty acids of the fatty acid mixture is lauric acid. According to another embodiment, the mixture of fatty acids includes coconut oil.

Considered a functional food, coconut oil is now being recognized by some of the healthcare community as a powerful intervention against immune system related diseases. Studies examining its effectiveness in this area, and additional research, are underway evaluating the nutritional value of pure coconut oil. Coconut oil is nutritious and contains lauric acid, which preliminary studies suggest is a disease fighting fatty acid. It is also rich in fiber, vitamins, and minerals. Coconut oil thus possesses abundant natural agents that may reduce fungus, pathogenic bacteria and the viruses that cause influenza, herpes, and other illnesses. The present invention incorporates the discovery that coconut oil is superior in enhancing nutrient absorption. While not being bound by any particular theory, it is believed that because coconut oil is rich in medium chain fatty acids (MCFAs), which are smaller than long chain fatty acids (LCFAs), they permeate cell membranes easily, and do not require lipoproteins or special enzymes to be utilized effectively by your body.

When coconut oil is used in the compositions of the present invention it thereby serves a dual role of providing a support matrix for the probiotic bacteria of the suppository and also as a means to promote absorption of the beneficial compounds produced by the probiotic bacteria.

According to another embodiment, the mixture of fatty acids contains shea butter. According to yet another embodiment, the mixture of fatty acids includes both coconut oil and shea butter. Preferably, the fatty acid mixture is supplied using coconut oil to thereby also take advantage of the health benefits of the lauric acid in coconut oil in addition to the ability of the coconut oil to coat the walls of the rectum or vagina to promote absorption of the other beneficial ingredients.

Essentially any pharmaceutically acceptable base material for the formulation of rectal or vaginal suppositories can optionally be used in combination with the fatty acid mixture to form the matrix material of the present invention. Examples of suitable pharmaceutically acceptable base materials for the matrix include, but are not limited to, excipients such as polyethylene glycol, hydrogels, cocoa butter, glycerinated gelatin, and the like.

Essentially any probiotic bacteria beneficial to the human microbiome are suitable for use with the present invention. Probiotic bacteria suitable for use with the suppository compositions of the present invention include, but are not limited to, *Lactobacillus rhamnosus* (including *L. rhamnosus* GG, HA-111 and HA-114), *Bifidobacterium lactis*, *Lactobacillus planetarium* (including *L. plantarium* WCFS1), *Lactobacillus acidophilus* (including *L. acidophilus* GG and strains MUH-41, O-61, L-1, 43121, DDS-1 and La-5), *Lactobacillus casei* (including *L. casei* GG), *Lactobacillus brevis*, *Bifidobacterium longum*, *Lactobacillus salivarius*, *Lactococcus lactis*, *Bifidobacterium bifidum*, *Bacillus coagulans*, *Lactobacillus bulgaricus*, *Lactobacillus gasseri*, and combinations thereof. In one embodiment, suppository compositions are provided containing one or more of *L. acidophilus*, *L. rhamnosis* HA-111, *L. rhamnosis* HA-114, *L. plantarium*, *Bifidobacterium bifidum*, *Bifidobacterium longum* and *L. salivarius*.

Compositions according to the present invention can also include other beneficial microorganisms native to the human colon. Therefore, according to one embodiment of the present invention, compositions of the present invention include species of *Archaea* microorganisms found in the human colon.

Suppository compositions according to the present invention will contain between about 0.5 and about 5 wt % probiotic bacteria. In one embodiment, suppository compositions are provided containing between about 1 and about 4 wt % of probiotic bacteria.

According to one embodiment, suppository compositions according to the present invention also contain between about 0.5 and about 20 wt % of vinegar, preferably apple cider vinegar. In one embodiment, suppository compositions are provided containing between about 5 and about 15 wt % of apple cider vinegar.

Apple cider vinegar is preferred because it comprises fermented juice from crushed apples. Like apple juice, it contains pectin; vitamins B1, B2, and B6; biotin; folic acid; niacin; pantothenic acid and vitamin C, which provide nourishment to the probiotic bacteria of the suppository. It also contains sodium, phosphorous, potassium, calcium, iron and magnesium. Studies indicate that apple cider vinegar also releases toxins from the liver.

According to one embodiment, suppository compositions according to the present invention contain between about 5 and about 35 wt % of sodium bicarbonate. In one embodiment, suppository compositions are provided containing between about 10 and about 30 wt % of sodium bicarbonate.

According to one embodiment, suppository compositions according to the present invention contain Vitamin C. Typical compositions contain between about 125 and 7500 IU of Vitamin C. In one embodiment, suppository compositions are provided containing between about 1000 and about 5000 IU of Vitamin C.

Suppository compositions according to the present invention optionally also contain other beneficial ingredients, as well as ingredients selected to coat the walls of the rectum or vagina and thereby promote the nourishment of the probiotic bacteria Accordingly, suppository compositions according to the present invention may optionally further include one or more anti-oxidant, anti-inflammatory or nutrient vitamins in addition to Vitamin C and the vitamins provided by the apple cider vinegar. Exemplary vitamins include Vitamin A (900 IU-2000 IU), Vitamin $B_6$ (2.0 mg-100 mg), Vitamin D (250 IU-5000 IU), Vitamin $K_2$ (MK7) (150 mcg), and combinations thereof. One or more anti-inflammatory nutritional supplements can also be added, examples of which include, but are not limited to, potassium, folic acid, L-carnitine, quercetin, magnesium, calcium, alpha-lipoic acid, fiber, omega-3 fatty acids, Nuclear factor-like-2 (NRF2) activators, L-glutathione, L-glutamate, gamma-aminobutyric acid (GABA), and the like.

In one embodiment, suppository compositions according to the present invention optionally further include other nourishment sources for the probiotic bacteria. Suitable nourishment sources include, but are not limited to, lactose, galactose, fructose, fructose oligosaccharides, isomaltose, inulin, dextrose, glucose, amylopectin, resistant starch, corn starch, oligosaccharides, combinations thereof, and the like. Suppository compositions according to the present invention can contain between about 1 and about 20 wt % of one or more of the nourishment sources. In one embodiment, suppository compositions are provided containing between about 5 and about 15 wt % of one or more of these nourishment sources.

Suppository compositions according to the present invention can also optionally contain from about 0.5 wt % up to about 25 wt % of one or more nutritional supplements selected from lemon juice, lactic acid, chamomile (fresh or oil), coenzyme Q-10, collagen, gelatin, green tea extract, rosemary leaf extract, oregano oil, curcumin, coffee, ginger, petroleum jelly, mineral oil, cocoa butter, shark liver oil, flax seed oil, sodium chloride, green barley, agrimony, aniseed-basil, aniseed-fennel, cayenne, *Echinacea*, garlic, honey, molasses, horseradish, lavender, marshmallow, olive oil, whole leaf olive extract, milk, peppermint, slippery elm, buttermilk, goldenrod, St. John's wort, uva ursi, yarrow, bee pollen, bee propolis, and the like. Salicin from White Willow Bark (*Salix alba*) can also be used. Additional substances, such as excipients, adjuvants, carriers, preservatives, and the like, may also be added, and are well known to persons skilled in the art.

The foregoing ingredients are combined and formed by conventional mixing to form a uniform homogenous mass that is then molded by conventional means into the shape of a suppository. Depending upon the ingredients chosen it may be necessary to refrigerate the product, or cooling may be necessary to solidify the matrix material. The suppositories are packaged within conventional blister packs in a similar manner that rectal suppositories available over the counter for use in those with hemorrhoids are packaged.

According to one embodiment the individual suppositories within a blister pack are all the same. In another embodiment up to seven different formulations are provided within a blister pack to provide a patient with a full spectrum of probiotic bacteria and nutrients over the course of a week so the patient receives the variety of bacteria organisms present in a healthy gut microbiome.

Compositions for rectal or vaginal delivery may also be formulated as cooling gels, gel capsules, hydrogels, hydrogel capsules, tablets, creams, ointments, freeze dried and as liquids for delivery with an enema syringe or with a syringe for vaginal irrigation, for delivery by tubing, or for delivery by rectal or vaginal applicators.

In an alternative embodiment, a hydrocarbon-based ointment composition is provided containing up to about 75 wt % petrolatum, up to about 15 wt % mineral oil, and up to about 5 wt % shark liver oil. A hydrocarbon cream product is provided based on approximately equal parts white petrolatum and glycerin.

Encapsulated formulations for delivery of precise quantities of live healthy bacteria measured to compliment, treat or assist with providing that which is missing in the intestinal mucosa of a diseased person with the ingredients described herein can be used to replace fecal transplants. In one embodiment, subcompartmentalized hydrogel capsules formulated to deliver probiotic bacteria from one subcompartment and other ingredients described herein in at least one other subcompartment are inserted high into the intestines through the anus by a method within the ability of a trained physician of ordinary skill specializing in this field.

The inert matrix material is the primary system for delivery of the probiotic bacteria within the suppository composition. The suppository composition is designed so that the inert matrix material melts and dissolves within the rectum or vagina to release a dispersion of the probiotic material in a secondary delivery system within a multi-compartment hydrogel capsule. In a multi-compartment system, the other compartment(s) contains other beneficial ingredients, that may include a mixture of fatty acids as well as nutrient ingredients selected to coat the walls of the rectum or vagina and thereby promote the nourishment of the probiotic bacteria.

According to one embodiment at least 50 wt % of the saturated fats of the mixture of fatty acids is lauric acid in the secondary delivery system. According to another embodiment, the mixture of fatty acids includes coconut oil. According to another embodiment, the mixture of fatty acids contains shea butter. According to yet another embodiment, the mixture of fatty acids includes both coconut oil and shea butter.

A multi-chamber dosage form 10 according to the present invention is depicted in the sole drawing FIGURE, and is a commercially available subcompartmentalized hydrogel capsule. A first chamber 12 contains one or more species of probiotic bacteria (not shown) dispersed within the fatty acid matrix 14, with an inner wall 15 separating the first chamber 12 from a middle chamber 20 containing in this embodiment salicin from White Willow Bark (*Salix alba*), an anti-inflammatory that is transformed in the body to salicylic acid, the active ingredient of aspirin. Aspirin is shown for purposes of illustration, and essentially any steroidal or non-steroidal anti-inflammatory compound can be used in place of aspirin. Furthermore, essentially any other active ingredient suitable for oral, rectal or vaginal delivery can be substituted for the anti-inflammatory compound. Middle chamber 20 is separated by wall 13 from second chamber 16 containing nutritional supplements 18 disclosed herein for the probiotic bacteria and for the existing microbiome. The capsules can be hard or soft and can be made from gelatin or vegetable materials. The encapsulated multi-chamber matrix can also be taken orally. The exterior wall 11 can be coated with an enteric coating formulated (not shown) to dissolve at a predetermined gastrointestinal location.

One method according to the present invention supplements and nourishes the microbiome of the lower gastrointestinal tract of a person by inserting the suppository composition of the present invention. The product is administered with a frequency and quantity typical for a probiotic treatment regimen. Typically, as done with probiotics taken orally on a daily basis the suppository delivery system may also be administered daily.

The vaginal route of administration is also important as noted by the growing trend is to swab babies-born by C section with the vaginal fluid from their mother. This is said to possibly give the baby a beneficial set of bacteria. In a vaginal birth, the baby ingests some of its first bacteria while in transit through the birth canal. Babies born by C section don't naturally get their mother's vaginal/anal bacteria and have to settle for the microbes living in the hospital environment.

Research suggests that it is a distinct disadvantage to C section babies as compared to babies born vaginally and makes these former babies more at risk for health issues that may include asthma, food allergies and hay fever and even obesity. Although there is some seeding of the fetal gut while in the uterus, the majority of the baby's bacterial seeding occurs during the vaginal birth process.

At New York University Hospital, within 2 to 3 minutes of their birth, the mouth, body and anus of some C section babies are swabbed with gauze that had been placed in the mother's vagina for approximately an hour before the birth. In this way, the newborn is exposed to the microbiome of the mother as it would have been had it been born vaginally.

However, this approach assumes that the mother's vaginal/anal microbiome is healthy. To insure a healthy vaginal/anal microbiome in the mother-to-be, the present invention provides a method in which pregnant women can use these suppositories in the prenatal period. By introducing a favorable microbiome, this may translate to a healthier microbiome being delivered by swabbing after birth to the C-section newborn as well as to the newborn born vaginally through the birth canal and being exposed to the mother's vaginal/anal microbiome.

The present invention can also be used to modify the microbiome of the vagina of a female by inserting into the vagina the suppository composition of the present invention that has been formulated to supplement this microbiome.

The following example illustrates a rectal/vaginal suppository product according to the present invention:

EXAMPLE

The following ingredients were blended together in the order they are listed to form a uniform homogenous paste: These measurements are based on a healthy maintenance of the mucosa. Measurements may increase or otherwise be adjusted if being used for treatment or to replace FMT.
Coconut oil—2.5 ml-5 ml
Probiotic Blend—270-350 mg:
   *L. acidophilus* DDS 1
   *Bifidobacterium lactis*
   *L. plantarum* WCFS1
   *L. casei* GG
   *L. rhamnosus* GG
   *L. brevis*
   *Bifidobacterium longum*
   *L. salivarius*
   *Strep. thermophilus*
   *Bifidobacterium bifido*
Chamomile (fresh)—0.7 ml-1.25 cc
Sodium bicarbonate—0.75 ml-1.25 cc
Apple cider vinegar—0.7 ml-1.25 cc The suppositories were prepared by placing each measured ingredient in a septic container and blending after each addition to create a smooth and homogenous mixture. The mixture was then placed into a conventional blister casing. Once the suppository is encased it will then be placed in a container for marketing and distribution. This process followed what is performed with rectal suppositories that are purchased over the counter for hemorrhoid management.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What I claim is:

1. A dosage form for the delivery of probiotic bacteria and nutritional supplements to the gastrointestinal tract to supplement and nourish the existing microbiome thereof, comprising a multi-chamber capsule comprising at least two chambers including a first chamber containing one or more species of freeze dried probiotic bacteria dispersed within a fatty acid matrix, wherein the fatty acid matrix comprises a mixture of fatty acids that are solid at room temperature and in a dry environment, but melts when at body temperature and in contact with the mucosa of the gastrointestinal tract, and a second chamber containing a source of nutrition for the probiotic bacteria and for the existing microbiome that is dispersed in a pharmaceutically acceptable matrix material, wherein the pharmaceutically acceptable matrix material is solid at room temperature and in a dry environment, but melts when at body temperature and in contact with the mucosa of the gastrointestinal tract.

2. The dosage form of claim 1, wherein the dosage form is an oral capsule.

3. The dosage form of claim 2, wherein said capsule is hard or soft.

4. The dosage form of claim 1, wherein the dosage form is a suppository.

5. The dosage form of claim 1, where said mixture of fatty acids comprises at least 90 wt % of saturated fatty acids.

6. The dosage form of claim 5, wherein at least 50 wt./wt. % of the saturated fatty acids of said mixture of fatty acids is lauric acid.

7. The dosage form of claim 1, wherein said mixture of fatty acids comprises coconut oil or shea butter.

8. The dosage form of claim 1, wherein said second chamber further contains one or more nutritional supplements selected from the group consisting of: Vitamin A, Vitamin B6, Vitamin D, Vitamin K2 (MK 1), potassium, folic acid, L-carnitine, quercetin, magnesium, calcium, alpha-lipoic acid, fiber, omega-3 fatty acids, Nuclear factor-like 2 (NRF2) activators, L-glutathione, L-glutamate and gamma-aminobutyric acid (GABA) dispersed within said matrix material.

9. The dosage form of claim 1, wherein said second chamber further contains one or more items selected from the group consisting of: lemon juice, lactic acid, chamomile, coenzyme Q-10, collagen, gelatin, green tea extract, lactose, galactose, fructose, isomaltose, dextrose, glucose, amylopectin, inulin, resistant starch, corn starch, oligosaccharides, rosemary leaf extract, fiber, oregano oil, curcumin, coffee, ginger, petroleum jelly, mineral oil, shark liver oil, flax seed oil, magnesium, calcium, potassium, sodium chloride, green barley, mint, agrimony, aniseed-basil, aniseed-fennel, cayenne, *Echinacea*, garlic, honey, molasses, horseradish, lavender, marshmallow, olive oil, milk, peppermint, slippery elm, buttermilk, goldenrod, St John's wort, uva ursi, yarrow, bee pollen and bee propolis dispersed within said matrix material.

10. The dosage form of claim 1, wherein said source of nutrition for the probiotic bacteria and for the existing microbiome comprises apple cider vinegar.

11. The dosage form of claim 1, wherein said probiotic bacteria comprise one or more bacteria species selected from the group consisting of: *Lactobacillus rhamnosus, Bifidobacterium lactis, Lactobacillus plantarum, Lactobacillus acidophilus, Lactobacillus casei, Lactobacillus brevis, Bifidobacterium longum, Lactobacillus salivarius, Lactococcus lactis, Bacillus coagulans, Lactobacillus bulgaricus, Lactobacillus gasseri, Lactobacillus lactis, Streptococcus thermophilus* and *Bifidobacterium bifidum*.

12. The dosage form of claim 1, wherein said matrix comprises one or more pharmaceutically acceptable ingredients selected from the group consisting of: polyethylene glycol, hydrogels, cocoa butter, glycerinated gelatin, petrolatum, mineral oil, shark liver oil and shea butter.

13. The dosage form of claim 1, wherein said mixture of fatty acids comprises coconut oil.

14. The dosage form of claim 1, wherein said probiotic bacteria are selected from the group consisting of bacteria beneficial to the human microbiome.

15. A suppository composition comprising:
   a multi-chamber capsule characterized by
   (a) a first chamber containing one or more species of freeze dried probiotic bacteria dispersed within a fatty acid matrix, and
   (b) a second chamber containing a source of nutrition for the probiotic bacteria and for the existing microbiome dispersed in a pharmaceutically acceptable matrix material,
   wherein the pharmaceutically acceptable matrix material is solid at room temperature and in a dry environment, but melts when at body temperature and in contact with the mucosa of the gastrointestinal tract,
   the first chamber and the second chamber being separated by at least one wall,
   wherein the suppository composition is adapted to be inserted into a rectum or vagina of a user and wherein the fatty acid matrix comprises a mixture of fatty acids that are solid at room temperature and in a dry environment, but which melts at body temperature when in contact with the mucosa of the rectum or vagina.

16. The dosage form of claim 15, wherein said mixture of fatty acids comprises coconut oil.

17. The dosage form of claim 15, wherein said source of nutrition for the probiotic bacteria and for the existing microbiome comprises apple cider vinegar.

* * * * *